US005403583A

United States Patent [19]

Liu et al.

[11] Patent Number: 5,403,583

[45] Date of Patent: Apr. 4, 1995

[54] **BACILLUS MEGETARIUM ATCC 55000 AND METHOD OF USE THEREOF TO CONTROL *R. SOLANI***

[75] Inventors: Zong Lin Liu, Urbana; James B. Sinclair, Savoy, both of Ill.

[73] Assignee: Research Corporation Technologies, Inc., Tucson, Ariz.

[21] Appl. No.: 988,985

[22] Filed: Dec. 11, 1992

Related U.S. Application Data

[63] Continuation of Ser. No. 477,011, Feb. 7, 1990, abandoned.

[51] Int. Cl.$^6$ .................... A01N 63/00; A61K 37/00; C12N 1/20

[52] U.S. Cl. .................... 424/93.46; 424/93.4; 435/252.5; 435/837; 504/117

[58] Field of Search .................... 424/93 K, 93 D; 504/117; 435/252.5, 837

[56] References Cited

PUBLICATIONS

Singh et al. *Indian Journal of Chemistry,* vol. 28B, pp. 996–998 Nov. 1989.

Islam, *B.J. of Plant Diseases and Protection,* 92(3) pp. 233–240 1985.

*Primary Examiner*—David M. Naff
*Assistant Examiner*—L. Blaine Lankford
*Attorney, Agent, or Firm*—Scully, Scott, Murphy & Presser

[57] ABSTRACT

The present invention relates to bacteria which can be used as biological control agents for soybean diseases such as those caused by the fungus *Rhizoctonia solani.* These biological control agents are specific strains of *Bacillus megaterium* and can also be used for enhancement of soybean plant growth and yield, as well as for the production of antibiotics directed toward crop fungal diseases.

14 Claims, 1 Drawing Sheet

BACILLUS MEGETARIUM ATCC 55000 AND METHOD OF USE THEREOF TO CONTROL *R. SOLANI*

This is a continuation of application Ser. No. 477,011, filed on Feb. 7, 1990, now abandoned.

FIELD OF INVENTION

The present invention relates generally to a biological control agent for certain crop fungal diseases. More particularly, the present invention relates to a bacterial strains of *Bacillus megaterium* de Bary which can be used as biological control agents for soybean diseases such as those caused by the fungus *Rhizoctonia solani* Kühn. The biological control agent contemplated herein can also be used for enhancement of soybean plant growth and yield, as well as for the production of antibiotics directed toward crop fungal diseases.

BACKGROUND OF THE INVENTION

The soybean, *Glycine max* (L.) Merrill, was domesticated by the farmers in the eastern half of northern China during the Shang dynasty (ca. 1700–1100 B.C.), and first introduced to North America in 1765 by Samuel Bowen, a seaman employed by the East India Company, from China via London to Savannah (in the colony of Georgia). He manufactured soy sauce and exported it to London. In 1851, soybeans were introduced into the midwestern U.S. by Dr. Benjamin F. Edwards, who gave them to J. H. Lea, of Alton, Ill., who planted them in his garden. By 1854, soybeans had been disseminated throughout the United States.

World oilseed production for 1987–88 was estimated at a record 202 million tons, with soybeans accounting for half the total crop. The United States produced 51.8 million tons of soybeans, representing over 51% of world production. Brazil had a record harvest of 18.5 million tons, and the People's Republic of China harvested 11.8 million tons. The fourth highest producer was Argentina with 8.5 million tons.

In 1987, the worldwide loss to soybean diseases was estimated at 10.3 million metric tons. Losses in the United States were estimated at 50–60 million dollars in 1986 (estimates vary, depending upon market price). More than 100 pathogens are known to affect soybeans; about 35 are important economically. Some of the most important are those that cause damage to the roots and crowns of soybeans. One of the most important root and crown rot diseases are those caused by *Rhizoctonia solani*. Rhizoctonia diseases, including pre- and post-emergence damping-off, root and stem decay, and leaf and bud blight, have been reported in all soybean-growing areas of the world. Pre- and post-emergence damping-off and root decay can reduce stands by as much as 50% and losses of up to 40% have been recorded in Brazil and the U.S. The causal fungus has a wide host range, which includes field crops, vegetables, ornamentals, and fruit crops.

Pre-emergence blight caused by *R. solani* occurs immediately after the seedling emerges from the seed. The sprouted seed is killed and decayed by the causal fungus. Damping-off can occur a few days after emergence. Reddish-brown lesions appear at the base of the seedling stem and on roots just below the soil line. These may enlarge into sunken lesions, which may girdle the stem. Lesions and cankers may so weaken the stem that plants break off in mid-season or die. Decay may continue intermittently throughout the growing season, with continuing death of plants. Infected plants that survive show some yield reduction.

*R. solani* is primarily a soil inhabitant and has excellent saprophytic ability. The fungus can overseason in the absence of the host, and colonizes all types of plant debris. Growth in soil depends on nutrient supply, soil moisture, temperature, pH, and competition from other soil microorganisms. The population of the fungus generally is distributed mainly in the upper 10 cm (centimeters) of the soil, decreasing with depth to about 50 cm below the surface. When environmental conditions are optimal for the fungus, disease severity is directly related to inoculum potential. An inoculum density of 100 ug of mycelia/gram of soil can cause severe disease in soybeans. The fungus produces pectolytic and proteolytic enzymes which play a role in disease pathology.

There is no natural resistance to *R. solani* in soybeans or any other crop. An integrated disease management program has been used heretofore against this fungus which includes agronomic practices as well as fungicide seed protectants. The seed protectants which may be used alone or in combination with other fungicides for this purpose are: quintozene (pentachloronitrobenzene, Terraclor) or carboxin (DCMO, Vitavax) . Both, but particularly quintozene, cause delayed emergence and growth of seedlings. An integrated disease management program is required, which would include the use of a suppressive biological control agent. The present invention details the use of such an agent, and in particular, the use of particular *Bacillus megaterium* strains as biological control agents for *R. solani*.

The agricultural use of *B. megaterium* has been previously reported for disease control in rice and cotton. Inhibition of *Drechslera oryzae,* which causes brown spot disease in rice, by *B. megaterium,* and subsequent control of the disease was reported with regular spraying of a bacterial suspension. In field studies, spraying with a suspension of *B. megaterium* reduced rice disease incidence and resulted in better growth and higher rice yields [Islam, K. Z., et al. (1985) Z. Pflkrankh. Pflschutz (Journal of Plant Diseases and Protection) 92:241–246]. The use of a suspension of *B. megaterium* reduced the number of cotton plants killed by *Phymatotrichum omnivorum,* cause of cotton root rot, by 25% with a resulting yield increase in lint of 24% over the control [Cook, C. G. , et al. (1987), Proc. Beltwide Cotton Production—Mechanization Research Conf. Memphis, p. 43–45.]

Antibiotic production from *B. megaterium* has been observed. Berdy (CRC *Handbook of Antibiotic Compounds,* Vols. I–XIV, CRC Press, Inc., Boca Raton, Fla., 1980–1987) reports production of such antibiotics as ansamitocin-PDM-O, bacimethrin, megacin, pentapeptide, homopeptides. These are proteide antibiotics having relatively low mammalian toxicity. Additionally, *B. megaterium* was reported to inhibit three fungal pathogens of the rice phylloplane with the active fungicidal component being an antibiotic with a lipopeptide and polyoxin nature [Islam, K. Z., et al. (1985) Z. Pflkrankh und Pflschutz 92:233–240].

A variety of other uses for *B. megaterium* and its metabolites have been reported, including oxidation of selenium, phosphate solubilization, production of vitamin $B_{12}$ in corn meal and the ability to degrade the herbicide metolachlor. The use of any *B. megaterium* strains to inhibit fungal growth, disease or infection in soybeans has not been described or reported.

In laboratory culture studies, one *B. megaterium* strain was found to oxidize selenium to selenite and a trace of selenate. This may be an important means of providing sufficient selenium to herbage to ultimately prevent selenium deficiency in animals [Sarathchandra, S. U., et al. (1981) *Science* 211:600–601]. A product, Phosphabacterin, from the U.S.S.R. and containing cells of *B. megaterium* var. phosphaticum, was used in the Soviet Union and Eastern Europe for the bacterization of crops to exploit the phosphate solubilization properties of the bacterium. Additional studies using the phosphate-solubilizing microorganisms on various crops in field studies were reported in India [Subba-Rao, N. S., (1982) in *Advances in Agricultural Microbiology* (N. S. Subbao-Rao, ed.) p. 219–242, Oxford Press, New Delhi: Oxford]. Various *B. megaterium* strains or isolates have been reported to produce vitamin $B_{12}$ in corn meal [Chung, H. J. et al. (1986) *J. Food Sci.* 51:1514–1517] or to degrade metolachlor [Saxena, A. et al. (1989) *Appl. Environ. Microbiol.* 53:340–396].

SUMMARY OF THE INVENTION

The present invention provides biological agents for control of certain fungal diseases found in soybeans and other crops. Moreover, these agents can also stimulate growth and yield in soybeans. Specifically, these agents are particular strains of *B. megaterium* that exhibit the property of inhibiting fungal pathogens of soybeans in a non-phytotoxic manner and may also produce one or more antibiotics. The use of these strains instead of current seed and soil treatment fungicides allows reduction of environmental contamination by such fungicides.

Another aspect of the present invention relates to a biological control agent which produces one or more antibiotics capable of inhibiting fungal pathogens of soybeans or other crops.

Still another aspect of the present invention is directed to an improved method for soybean crop fungal disease control and compositions useful in treating fungal diseases.

DETAILED DESCRIPTION OF THE INVENTION

Figure 1A:
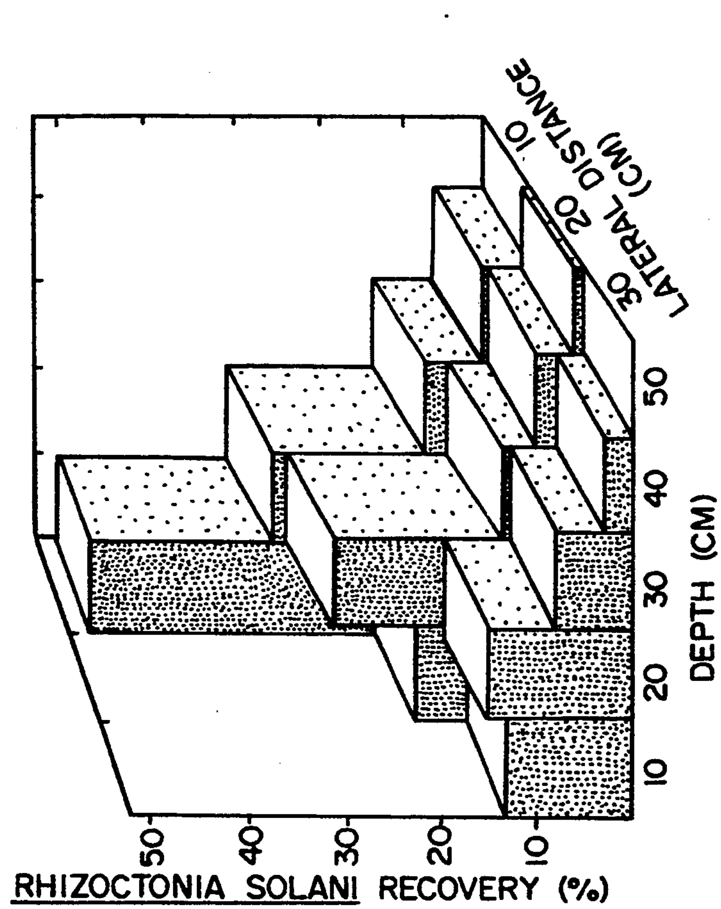
FIGS. 1A and 1B are graphical representations of the percentage recovery of the fungal pathogen *R. solani* remaining in the soybean root rhizosphere after treatment with a *B. megaterium* isolate (FIG. 1B) or after no treatment (FIG. 1A) .

The present invention relates to a biological agent for the control of fungal disease in soybeans. More specifically, the present invention relates to *B. megaterium*, strains which can be used as control agents against diseases caused by *R. solani* in soybeans. Such strains of *B. megaterium* have been isolated from a group of naturally-occurring isolates of Bacillus, and do not require genetic alteration for use as effective biological control agents.

The unexpected and surprising attributes of these specific *B. megaterium* strains as biological control agents include the following characteristics. The strains have a rapid generation time in culture (28 minutes at 30° C.) and a rifampicin-resistant marker, which provides a means to monitor the microorganism in the field or elsewhere. In pure culture these agents inhibit the growth of most fungal pathogens of soybeans, without being phytotoxic to soybeans or zoopathogenic. A pure culture or a cell-free culture supernatant of these *B. megaterium* strains can inhibit the vegetative growth of *R. solani*, a pathogen which causes the Rhizoctonia diseases of soybean crowns, roots, hypocotyls and stems. The *B. megaterium* strains of the present invention have a rapid growth rate, are capable of colonizing the soybean root system, can survive in the soybean root rhizosphere, and can overwinter in the field at temperatures as low as about 0° to about −10° C. in the soil. These bacteria reduce the diseases caused by *R. solani* in soil both under greenhouse conditions and in the field. Moreover, the present strains continue to survive in the soil during the growing season and show sustained antagonism to the pathogen *R. solani*.

The subject *B. megaterium* strains can also stimulate lateral root production on soybean plants under controlled environmental conditions and in the field. Such agents are further capable of stimulating the production of nitrogen-fixing nodules on soybean plants in the field. The nodules are typically produced by another bacterium, *Bradyrhizobium japonicum*, but these agents further stimulate the production of nodules. In addition, these bacterial strains appear to produce one or more antibiotics which inhibit *R. solani* or other fungal pathogens of soybeans since culture supernatants and cell-free culture filtrates exhibit growth inhibitory effects for *R. solani*.

The subject *B. megaterium* strains have the taxonomic characteristics listed in Table 1, as compared to those of *B. subtilis* and the prior art strains of *B. megaterium*.

TABLE 1

Comparisons of biochemical and physical characteristics of *Bacillus megaterium* isolate B153-2-2 (invention), *Bacillus megaterium* (descriptive) and *Bacillus subtilis* (descriptive).

| | *Bacillus megaterium* | | *Bacillus subtili* |
|---|---|---|---|
| Characteristic | Invention | Descriptive[v] | Descriptive[v] |
| Gram reaction | +(w) | + | + |
| Motility | + | + | + |
| Catalase reaction | + | + | + |
| Anaerobic | −(x) | − | − |
| Voges-Proskauer (V-P) | − | − | + |
| Maximum temperature | 50° C. | 45° C. | 55° C. |
| Minimum temperature | 15° C. | 15° C. | 15° C. |
| NaCl-5% | + | 0 (y) | + |
| NaCl-7% | + | + | + |
| NaCl-10% | + | 0 | + |
| Medium pH 5.7 | + | + | + |
| Acid from glucose | + | + | + |
| Pigment on tyrosine | + | +/−(z) | − |
| Starch hydrolysis | + | + | + |
| Citrate utilization | + | + | + |
| Propionate utilization | + | + | − |
| Nitrate to nitrite | + | +/− | + |
| Casein decomposition | + | + | + |
| Tyrosine decomposition | + | +/− | − |
| Litmus milk | Alkaline | Alkaline | Alkaline |
| Lysozyme | + | + | − |
| pH in V-P broth | 7.5 | 4.5–6.8 | 6.5–7.0 |
| Unstained globules | + | + | − |
| Cell width | 1.2–1.3 um | >1 um | <1 um |

v = As described in: Gordon R.E., Haynes, W.C., and Hor-Nay Pang, C. 1973. The Genus Bacillus USDA, ARS Agr, Handbook No. 427, U.S. Dept., Agr. Res. Sv., Washington, D.C., 283 pp.
w = Positive reaction
x = negative reaction
y = not available
z = reaction variable A representative isolate of the strains of the present invention has been deposited with the American Type Culture Collection, 12301 Parklawn Drive, Rockville, Md. 20852. This isolate is *B. megaterium* strain B153-2-2 assigned accession number ATCC 55000.

In addition to the other properties noted above, these novel *B. megaterium* strains also have the following qualities which are important for use as a biological control agents for soybean crop root pathogens by:

a) being a naturally-occurring isolate or strain of a nonplant-parasitic microorganism that does not require genetic alteration to be effective,
b) being easily cultured and having a rapid generation time in culture,
c) exhibiting rapid initial growth rate in the field,
d) having a stage in its life cycle that is resistant to harsh environmental conditions,
e) being suppressive to one or more soybean root plant pathogens in the field,
f) being relatively easy to develop for commercial purposes,
g) reducing the population of a soybean root pathogen(s) in the filed,
h) reducing symptoms of fungal disease(s) on the host soybean crop in the field,
i) colonizing the root system of the host soybean plant(s) for the pathogen(s) involved,
j) colonizing the rhizosphere of the root system of the host soybean plant(s),
k) remaining in the soil for the full growing season,
l) being non-phytotoxic to the host soybean plant(s),
m) enhancing the root growth of the host soybean plant(s),
n) enhancing the yield of the host soybean plant(s), and
o) not adversely affecting nodule formation, in the soybean plants, but rather promoting Bradyrhizobium-induced nodule formation in such plants.

Another aspect of this invention is directed to a method of controlling fungal diseases in soybean crops, especially to controlling diseases caused by *R. solani.* Crops are treated pre-emergence or post-emergence of the seedling with a fungicidally effective amount of the *B. megaterium* strains of the present invention. The *B. megaterium* B153-2-2 strain designated ATCC 55000 is especially preferred in this process.

The term "fungicidally effective" amount is defined herein to be the population of the subject *B. megaterium* strain inoculum required to reduce the pathological effects of fungal pathogens and to obtain the desired population of the subject *B. megaterium* strain in the soil and on the plant.

Treatment on a pre-emergence basis includes treatment of soybean seeds from any time prior to implantation up to the appearance of a seedling. Post-emergence treatment then encompasses treatment after the seedling appears above the soil.

The present method may be used with soybean crops or plants grown in the greenhouse or in the field. An inoculant of the subject strains is used such that colonization in the range of about $10^3$–$10^8$ colony forming units/gram (cfu/g) soil occurs and preferably about $10^4$–$10^7$ cfu/g. The inoculant can be applied directly to the seeds or plants, can be present in the soil before planting or can be distributed, e.g. by spreading dusting or the like, over the crop or soil where the crop has been planted.

Seeds can be treated by coating with a composition containing the subject bacteria by dipping in a liquid containing these bacteria, by spraying with the liquid, or other method known in the art for applying bacteria to seeds.

When present in peat, the bacteria are grown in broth to the necessary amount, then concentrated and mixed with peat or soil at the desired inoculum. Optionally this mixture may be cured by well known methods to form a granular peat composition.

The carriers that may be used to disperse the subject strains on a pre- or post-emergence basis would include all those commonly used for dispersing fungicides on soybean crops and would include carriers such as water, clay, talc and other dusting agents. The bacteria in such compositions are at a level of about $10^3$–$10^8$ cfu/g carrier, especially $10^4$–$10^8$ cfu/g or $10^7$–$10^8$ cfu/g, provided that concentration is a fungicidally effective amount for the composition in question.

Any of the above compositions, liquids, powders, peat, soil and the like may have nutrients included therein or appropriate carrier medium such as water, oils or solid bases such as powders, peat, soil, clay, talc and any other dusting agents.

The following example serves to further illustrate this invention without limiting the same.

EXAMPLE

A collection was made of Bacillus species from soybean leaves, stems, crowns, and roots, as well as from soil of a field in soybean monoculture for over 25 years. Five *B. megaterium* isolates were obtained which were antagonistic to *R. solani,* but not phytotoxic to soybeans. One *B. megaterium* isolate was selected from this group, for further investigation of its properties. This isolate is the *B. megaterium* B153-2-2 strain designated ATCC 55000 and it showed a strong ability to suppress *R. solani* and symptoms caused by *R. solani* on soybeans in the greenhouse and the field.

This isolate has the above noted taxonomic characteristics and in addition contains a rifampicin-resistance marker so that its colonization of soybean roots can be monitored in greenhouse and field studies.

Seedlings from soybean seeds treated with a suspension of the isolate in water were grown in a greenhouse in soil infected with *R. solani* and had a significantly ($P=0.05$) lower disease index and number of lesions/seedling than those from untreated seeds (Table 2).

Figure 1B:
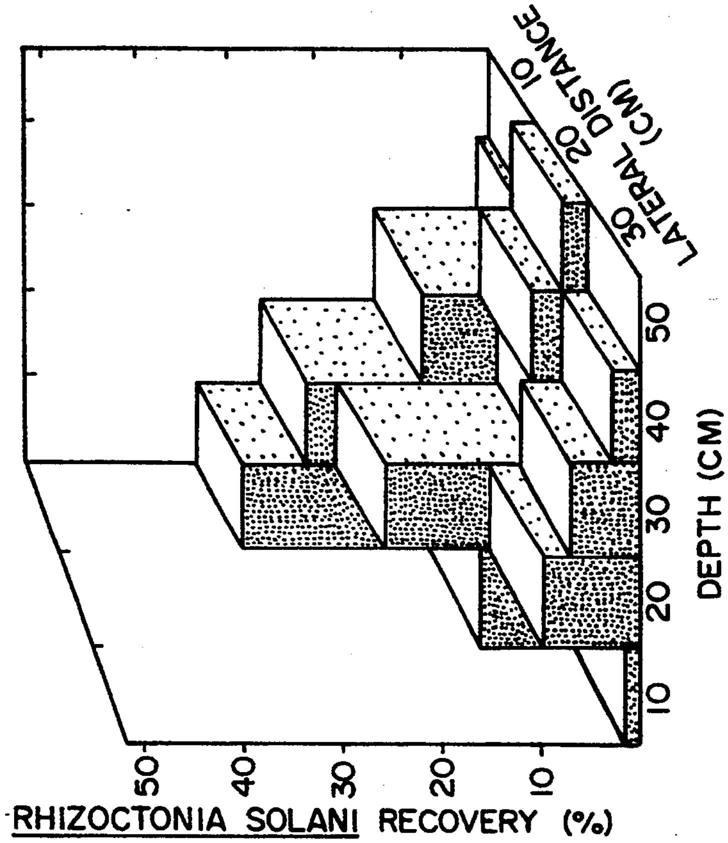

Field application of this isolate (ATCC 55000) in Illinois showed a significantly improved soybean seedling stand compared with untreated soybean seedlings infested with *R. solani. R. solani* was recovered significantly less often from soil planted with soybean seeds treated with the isolate than from soil planted with untreated soybean seeds as illustrated in FIGS. 1A and 1B. The field application of the ATCC 55000 strain was carried out using a composition containing about $10^7$–$10^8$ cfu/g of soybean stem powder as a carrier. A range of about 8 to 10 pounds of this composition can be applied per acre of crop area.

Colonization of soybean roots by ATCC 55000 extended to 20 cm below and 5 cm above the soil line using bacterium-coated soybean seeds. The highest populations of the isolate found on the plant were about $1.2\times10^8$ cfu/g fresh root and occurred at 5 cm below the soil line. In the field, this bacterium was recoverable at a distance of at least 30 cm horizontally and at least 50 cm vertically from the application site at about 30 to 40 days after application. Maximum rhizosphere population recovered was $4\times10^7$ cfu/g soil, and the minimum rhizosphere population recovered was about $10^4$ cfu/g soil at about 100 to 120 days after application.

The population of this strain was high at the beginning of the season and decreased toward the end of the growing season. It remained stable and similar in population to that of naturally-occurring Bacillus species throughout the winter. A population base of about $8\times10^4$ ($\pm10^1$) cfu/g soil was needed for survival. The presence or absence of *R. solani* did not affect colonization on roots or in the rhizosphere.

Root volume and dry weight of plants treated with the ATCC 55000 strain was significantly higher than those of untreated plants or plants treated with *B. subtilis* strain CA8 (Table 2). There was also a significant increase in nodulation by *Bradyrhizobium japonicum* observed in plants treated with this isolate. Soil application resulted in a significant increase in yield as compared to treatment with *R. solani* alone or *R. solani* and the ATCC 55000 strain.

TABLE 2

Comparison of the biocontrol potential of *B. megaterium* isolate ATCC 55000 and *B. subtilis* isolate CA8 against the soybean fungal pathogen *R. solani* on soybeans in the greenhouse.

| Treatment | Lesion no. | Disease index (%) | *R. solani* Recovery (%) | Root vol. (ml) | Root wt. (mg) | Plant dry wt. (mg) |
|---|---|---|---|---|---|---|
| *R. solani* | 13.2 | 82.3 | 94.0 | 352.5 | 45.6 | 193.1 |
| *R. solani* + ATCC 55000 | 8.9*/[a] | 70.5* | 81.0* | 472.5* | 54.2 | 231.9* |
| *R. solani* + CA8 | 9.9 | 71.0 | —[b] | 445.0 | 40.8 | 165.2 |

[a] = Number followed by an asterisk is significantly different compared with the treatment with *R. solani* alone.
[b] = No data.

What is claimed is:

1. A biologically pure culture of *Bacillus megaterium* ATCC strain 55000, or mutants thereof, wherein said mutants are capable of controlling the soybean pathogen *R. solani* without phytotoxic effects on the soybean plant.

2. The strain of claim 1 which stimulates lateral root production and production of nitrogen fixing nodules on soybean plants.

3. The strain of claim 1 which is adapted to overwinter in the field at temperatures of from about 0° C. to about 10° C.

4. The strain of claim 1 which inhibits a *Rhizoctonia solani* fungal pathogen.

5. A composition comprising a fungicidally effective amount of a cultured *Bacillus megaterium* ATCC strain 55000 and a carrier therefor.

6. The composition of claim 5 wherein said fungicidally effective amount of said strain comprises about 8 to about 10 pounds per acre of about $10^3$ to about $10^8$ colony forming units of said strain per gram of carrier.

7. The composition of claim 5 wherein said fungicidally effective amount of said strain comprises about 8 to about 10 pounds per acre of about $10^7$ to about $10^8$ colony forming units of said strain per gram of carrier.

8. The composition of any one of claims 5–7 wherein said carrier is soybean stem powder.

9. A method for control of *R. solani* fungus in a soybean crop which comprises pre-emergence or post-emergence treatment of said crop with a fungicidally effective amount of a *Bacillus megaterium* ATCC strain 55000.

10. The method of claim 9 wherein said fungicidally effective amount of said strain comprises about 8 to about 10 pounds per acre of about $10^3$ to about $10^8$ colony forming units of said strain per gram of carrier.

11. The method of claim 9 wherein said fungicidally effective amount of said strain comprises about 8 to about 10 pounds per acre of about $10^7$ to about $10^8$ colony forming units of said strain per gram of carrier.

12. The method of claim 10 or 11 wherein said carrier is soybean stem powder.

13. The method of claim 9 wherein said *Bacillus megaterium* strain stimulates the production of lateral roots and nitrogen fixing nodules on soybean plants.

14. The method of claim 9 wherein said *Bacillus megaterium* strain is adapted to overwinter in the field at soil temperatures of from about 0° C. to about −10° C.

* * * * *

UNITED STATES PATENT AND TRADEMARK OFFICE

CERTIFICATE OF CORRECTION

PATENT NO. : 5,403,583

DATED : April 4, 1995

INVENTOR(S) : Zong Lin Liu, et al.

It is certified that error appears in the above-indentified patent and that said Letters Patent is hereby corrected as shown below:

Column 1, line 4, insert the following: --This invention was made with Government support under Hatch (ILLU 68-0346) awarded by the U.S. Department of Agriculture. The Government has certain rights in the invention.--

Column 4, line 37: "subtili" should read --subtilis--

Column 5, line 21: "filed" should read --field--

Signed and Sealed this

Twenty-first Day of May, 1996

Attest:

BRUCE LEHMAN

Attesting Officer

Commissioner of Patents and Trademarks